United States Patent
Felix et al.

(10) Patent No.: US 8,092,503 B2
(45) Date of Patent: Jan. 10, 2012

(54) POLYAXIAL SCREW SYSTEM

(75) Inventors: Brent A. Felix, Sandy, UT (US); Christian L. Lauridsen, Woodland Hills, UT (US); Keith R. Peterson, Orem, UT (US)

(73) Assignee: Innovasis, Inc., Salt Lake City, UT (US)

( * ) Notice: Subject to any disclaimer, the term of this patent is extended or adjusted under 35 U.S.C. 154(b) by 513 days.

(21) Appl. No.: 12/270,556

(22) Filed: Nov. 13, 2008

(65) Prior Publication Data

US 2009/0287253 A1 Nov. 19, 2009

Related U.S. Application Data

(60) Provisional application No. 61/053,545, filed on May 15, 2008.

(51) Int. Cl.
*A61B 17/70* (2006.01)
(52) U.S. Cl. .......... 606/267; 606/264; 606/278
(58) Field of Classification Search .......... 606/246, 606/254–262, 264–270, 272, 277, 278, 300, 606/301, 305, 309, 328
See application file for complete search history.

(56) References Cited

U.S. PATENT DOCUMENTS

| | | | |
|---|---|---|---|
| 4,648,388 A * | 3/1987 | Steffee | 606/261 |
| 5,466,237 A | 11/1995 | Byrd, III et al. | |
| 5,474,555 A | 12/1995 | Puno et al. | |
| 6,063,090 A | 5/2000 | Schlapfer | |
| 6,248,105 B1 | 6/2001 | Schlapfer et al. | |
| 6,280,442 B1 | 8/2001 | Barker et al. | |
| 6,371,957 B1 | 4/2002 | Amrein et al. | |
| 6,471,705 B1 | 10/2002 | Biedermann et al. | |
| 6,565,567 B1 | 5/2003 | Haider | |
| 6,641,586 B2 | 11/2003 | Varieur | |
| 6,660,004 B2 | 12/2003 | Barker et al. | |
| 6,740,086 B2 | 5/2004 | Richelsoph | |
| 7,578,833 B2 * | 8/2009 | Bray | 606/246 |
| 2006/0085072 A1 | 4/2006 | Funk et al. | |
| 2006/0089644 A1 * | 4/2006 | Felix | 606/61 |
| 2006/0149231 A1 * | 7/2006 | Bray | 606/61 |
| 2006/0293659 A1 * | 12/2006 | Alvarez | 606/61 |
| 2007/0173817 A1 * | 7/2007 | Sournac et al. | 606/61 |

OTHER PUBLICATIONS

*VLS System Variable Locking Screw*, Interpore Cross International, 2001.
EBI Spine Systems, *EBI Ωmega21 Fixation System, Surgical Technique*, published at least as early as Sep. 1, 2006.
*Click'X Top Loading System, Technique Guide*, Synthes Spine 2003.
*Synergy IQ, Low Surgical Technique*, Interpore Cross International, 2003.

* cited by examiner

*Primary Examiner* — Eduardo C Robert
*Assistant Examiner* — Ellen C Hammond
(74) *Attorney, Agent, or Firm* — Workman Nydegger

(57) ABSTRACT

A polyaxial screw system includes a drive cap having a partition wall with a first side and an opposing second side, a passage extending through the partition wall. A sleeve projects from the second side of the partition wall, the sleeve and partition wall bounding a socket. A shaft outwardly projects from the first side of the partition wall. A screw has a threaded portion and a head formed on an end thereof. The head of the screw is at least partially disposed within socket of the drive cap. A collet is at least partially disposed within the socket of the drive cap. At least a portion of a compression cap movably extends through the opening in the partition wall so that the compression cap can selectively move the collet relative to the drive cap.

19 Claims, 12 Drawing Sheets

POLYAXIAL SCREW SYSTEM

CROSS-REFERENCE TO RELATED APPLICATIONS

This application claims the benefit of U.S. Provisional Application Ser. No. 61/053,545, filed May 15, 2008, which application is incorporated herein by specific reference.

BACKGROUND OF THE INVENTION

1. The Field of the Invention

The present invention relates to polyaxial screw systems that can be used for stabilizing adjacent vertebrae of the spine or other adjacent bones. The polyaxial screw system can be used with a rod clamp, plate, or other stabilizing structures.

2. The Relevant Technology

Polyaxial screws are commonly used in spinal operations for adjusting or stabilizing adjacent vertebrae. For example, in one conventional procedure a first polyaxial screw is screwed into a first vertebrae while a second polyaxial screw is screwed into an adjacent second vertebrae. A stabilizing rod is then secured between the polyaxial screws so as to fix the adjacent vertebrae relative to each other. Polyaxial screws can be positioned on each side of each vertebrae and can be positioned in any number of consecutive vertebrae with one or more rods extending between the different polyaxial screws.

One conventional polyaxial screw comprises a bone screw having a U-shaped collar pivotably mounted on the end thereof. The stabilizing rod is received within a U-shaped slot of the U-shaped collar and secured therein by a set screw being threaded into the U-shaped slot of the collar and biased against the rod. Although such systems are functional, they have certain drawbacks. For example, as a result of the collar being U-shaped, there is some risk that the collar will outwardly flare and thus fail as the set screw is threaded into the U-shaped slot and secured against the rod.

An additional problem with the above conventional polyaxial screw is that due to the specialized configuration of the U-shaped collar, the screw can only be used directly with a stabilizing rod. In some cases, based on the situation or surgeons preference, it may be desirable to use plates or other non-rod stabilizing structures to extend between the polyaxial screws. Accordingly, what is needed are polyaxial screw systems that overcome some or all of the above disadvantages.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

Figure 1:
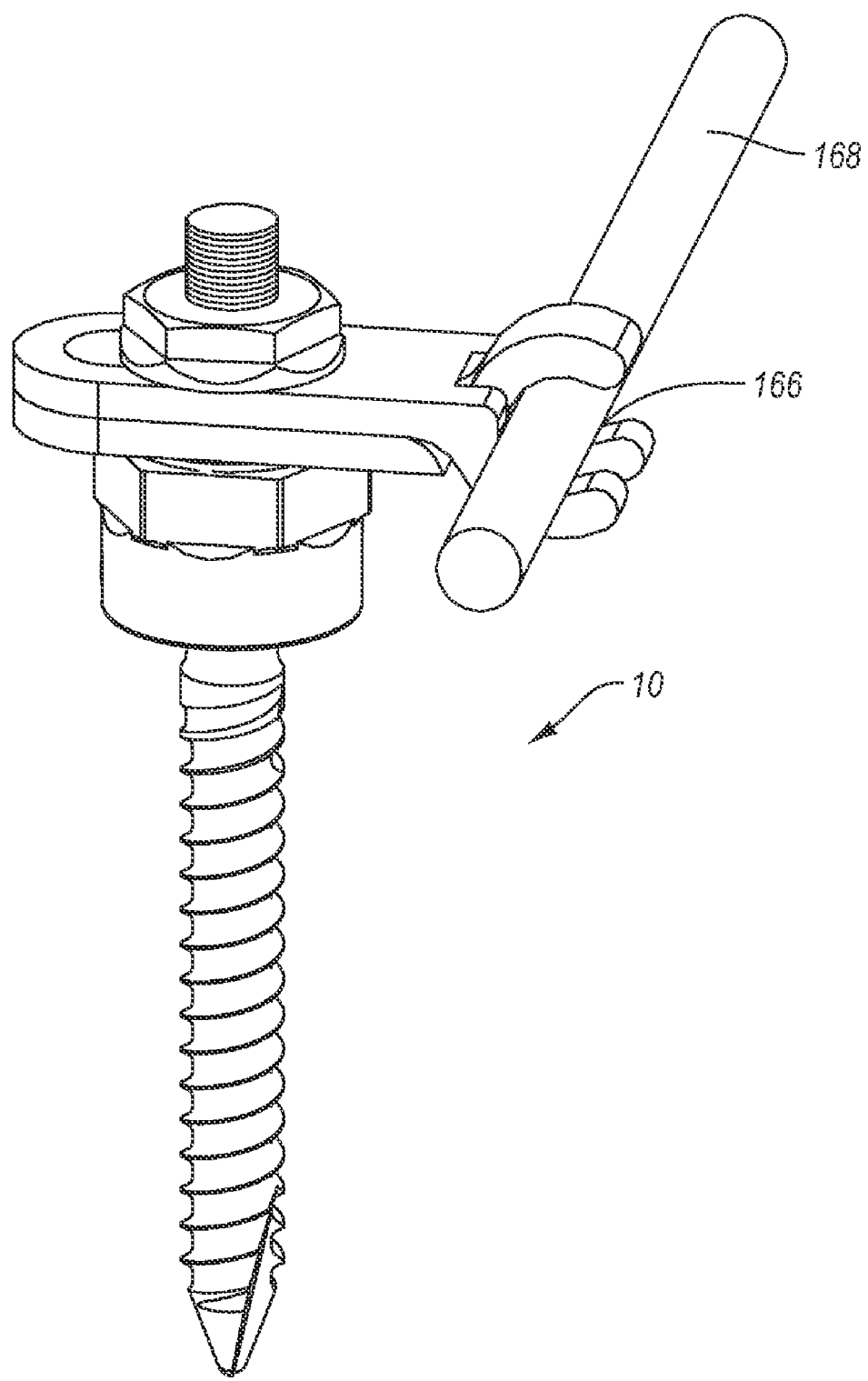
FIG. 1 is a perspective view of one embodiment of a polyaxial screw system of the present invention used with a stabilizing rod.

Depicted in FIG. 1 is one embodiment of a polyaxial screw system 10 incorporating features of the present invention. In one embodiment polyaxial screw system can be used for stabilizing adjacent vertebrae of a spine as part of a procedure for fusing together the adjacent vertebrae. Polyaxial screw system 10 can also be used for stabilizing a series of consecutive vertebrae for manipulation of the spine to correct spinal deformities such as scoliosis. It is appreciated that polyaxial screw system 10 and/or discrete elements thereof can also be used in other procedures for anchoring, manipulating, and/or stabilizing portions of the spine or other bones.

Figure 2:
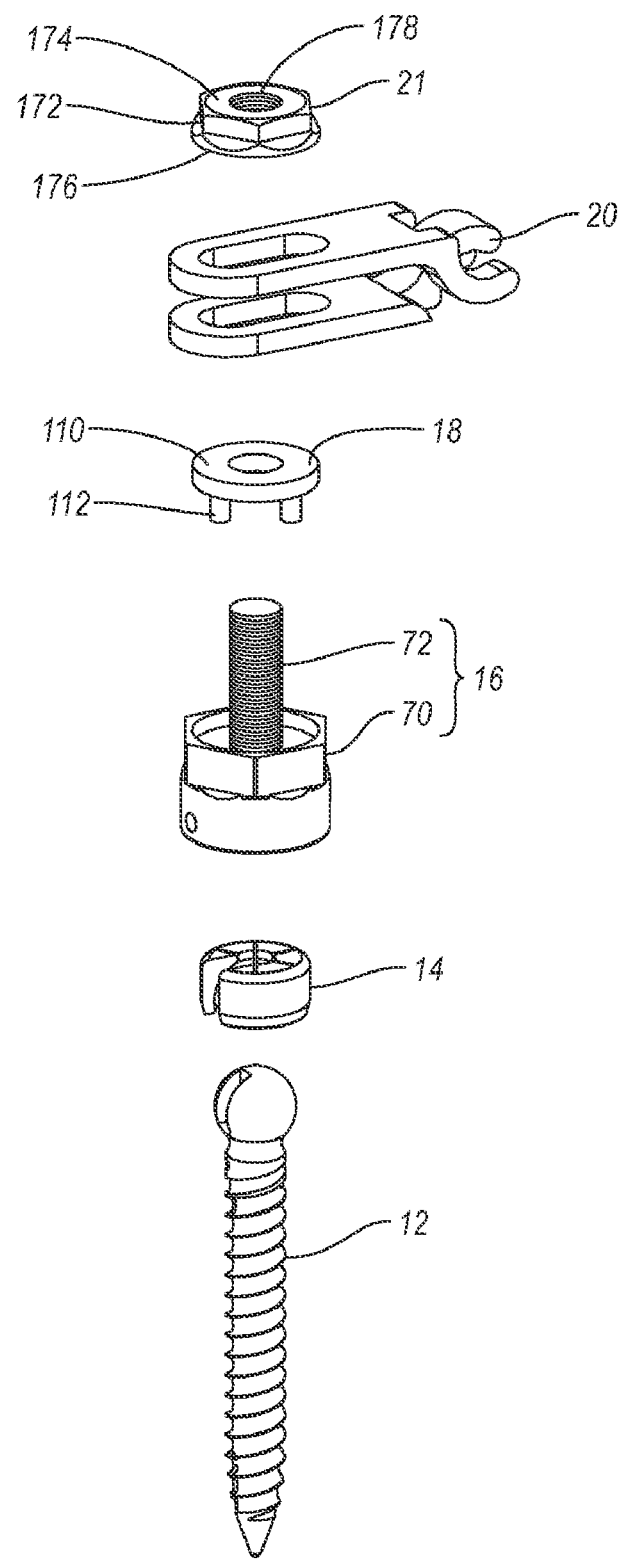
FIG. 2 is an exploded perspective view of the polyaxial screw system shown in FIG. 1.

As depicted in FIG. 2, polyaxial screw system 10 comprises an elongated screw 12, a collet 14, a drive body 16, a compression cap 18, a stabilizing member, which in the depicted embodiment includes a rod clamp 20, and a fastener 21. The above identified components and their relative interaction will now be discussed in greater detail.

Figure 3:
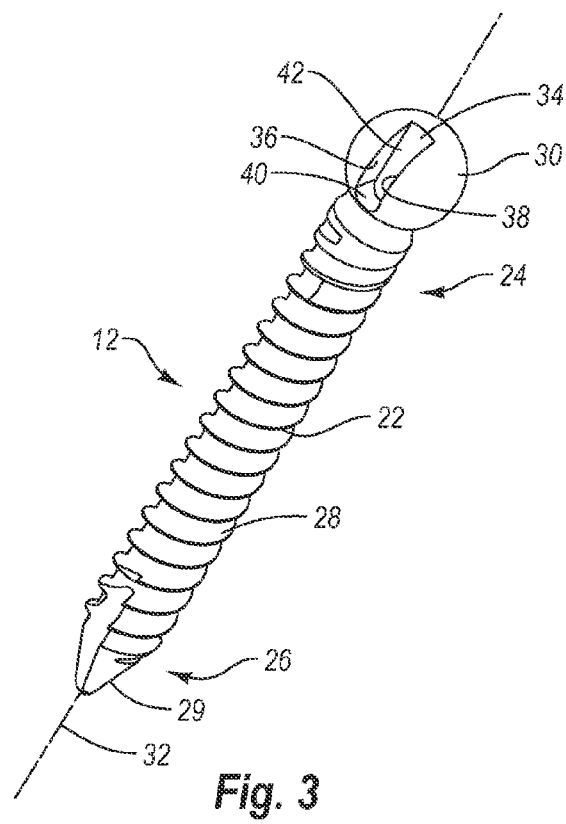
FIG. 3 is a perspective view of the bone screw shown in FIG. 2.

Turning to FIG. 3, screw 12 comprises an elongated shaft 22 having a first end 24 and an opposing second end 26. One or more threads 28 helically encircle and radially outwardly project from shaft 22 along the length thereof. The one or more threads 28 can have a variety of different pitches and configurations, and, if desired, can be self tapping. Although not required, second end 26 terminates at a tapered tip 29 having a substantially conical configuration for ease in penetration into a bone or predrilled hole. In contrast to second end 26, an enlarged head 30 is disposed at first end 24 of shaft 22. Shaft 22 has a central longitudinal axis 32 which centrally extends through tip 29 and head 30.

Figure 15:
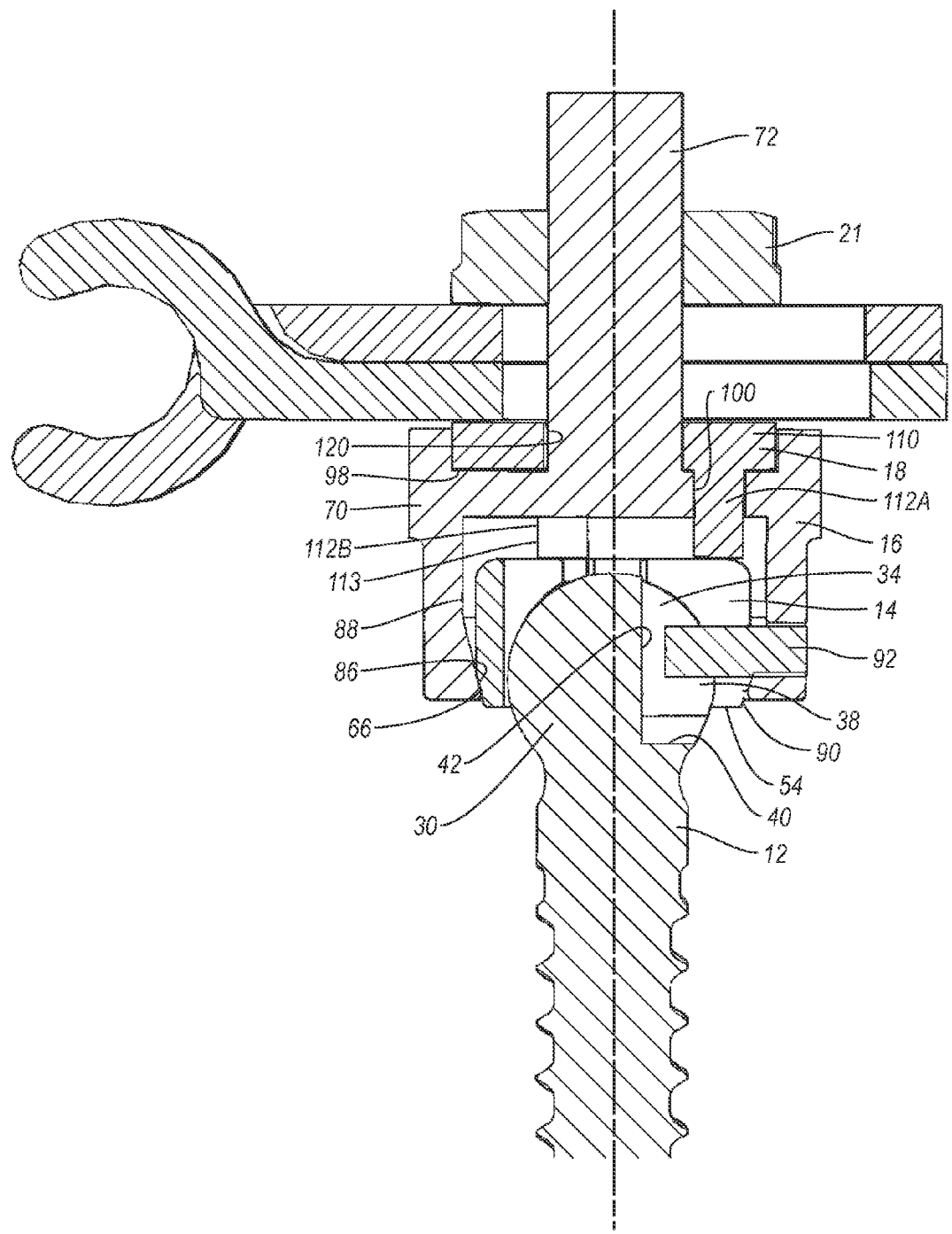
FIG. 15 is a cross section side view of the polyaxial screw system shown in FIG. 14 with the drive body in a locked position.

Although not required, in the embodiment depicted head 30 has a substantially spherical configuration. An engagement slot 34 is formed on head 30. Engagement slot 34 comprises a pair of opposing side walls 36 and 38 that are generally disposed and parallel plains and that extend to a floor 40 and a back wall 42. As depicted in FIG. 15, back wall 42 typically intersects with floor 40 at a right angle while back wall 42 is disposed generally parallel to central longitudinal axis 32 at a distance space apart therefrom. It is appreciated that slot 34 can have a variety of different configurations and merely needs to be sized, shaped, and oriented to permit the desired pivoting of drive body 16 and rotation of screw 12 as will be discussed below in greater detail.

Figure 4:
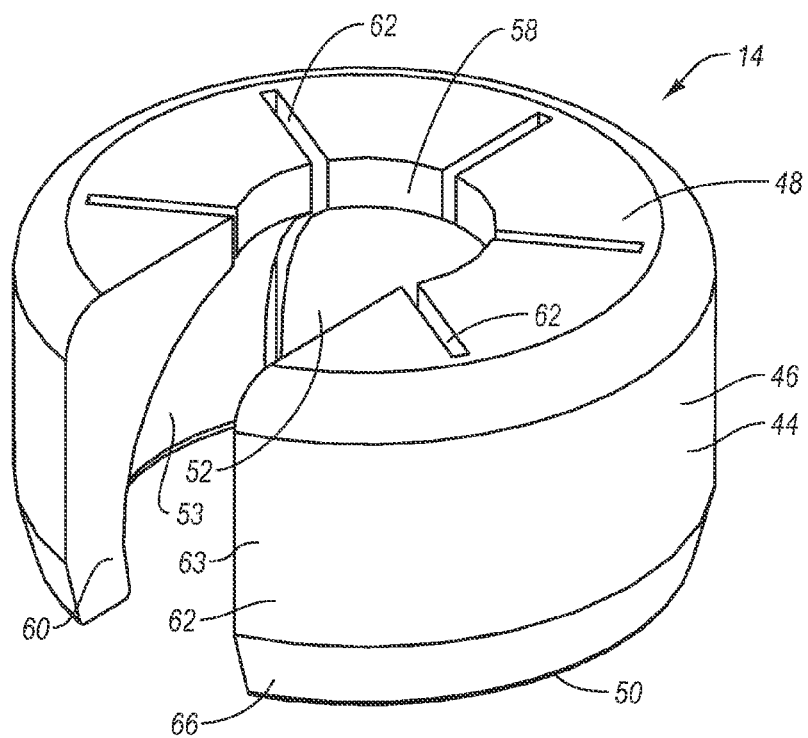
FIG. 4 is a top perspective view of the collet shown in FIG. 2.
Figure 5:
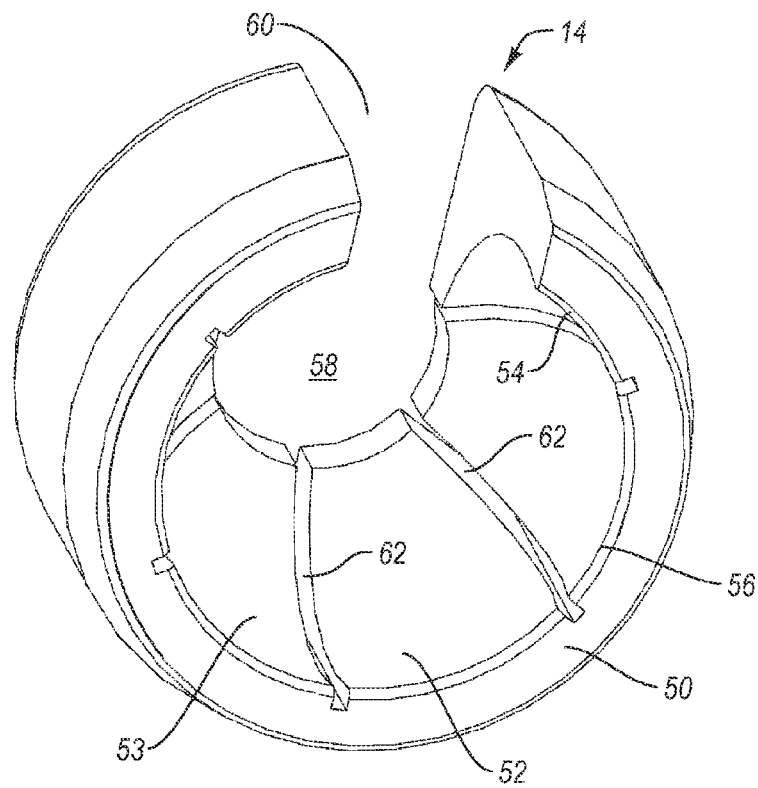
FIG. 5 is a bottom perspective view of the collet shown in FIG. 4.
Figure 6:
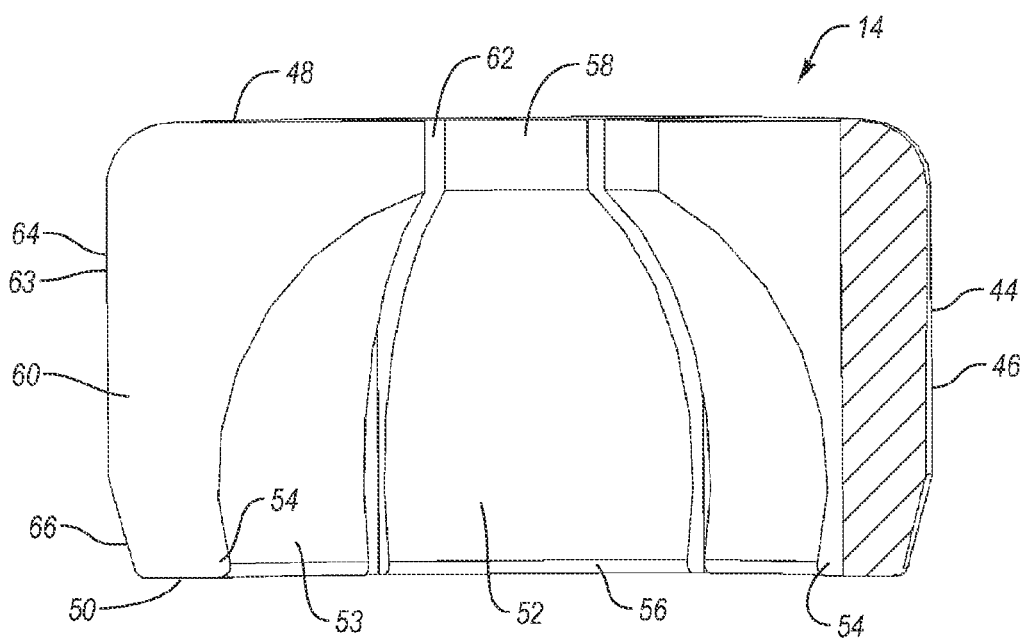
FIG. 6 is a cross sectional side view of the collet shown in FIG. 4.

Depicted in FIGS. 4-6, collet 14 comprises a substantially disk-shaped body 44 having a side wall 46 that extends between a first end wall 48 and an opposing second end wall 50. End walls 48 and 50 are disposed in substantially parallel planes. Side wall 46 has an exterior surface 63 that comprises an upper face 64 disposed toward first end wall 48 that encircles body 44 having a substantially cylindrical configuration and a beveled face 66 disposed toward second end wall 50 that encircles body 44 and slopes inwardly.

Figure 14:
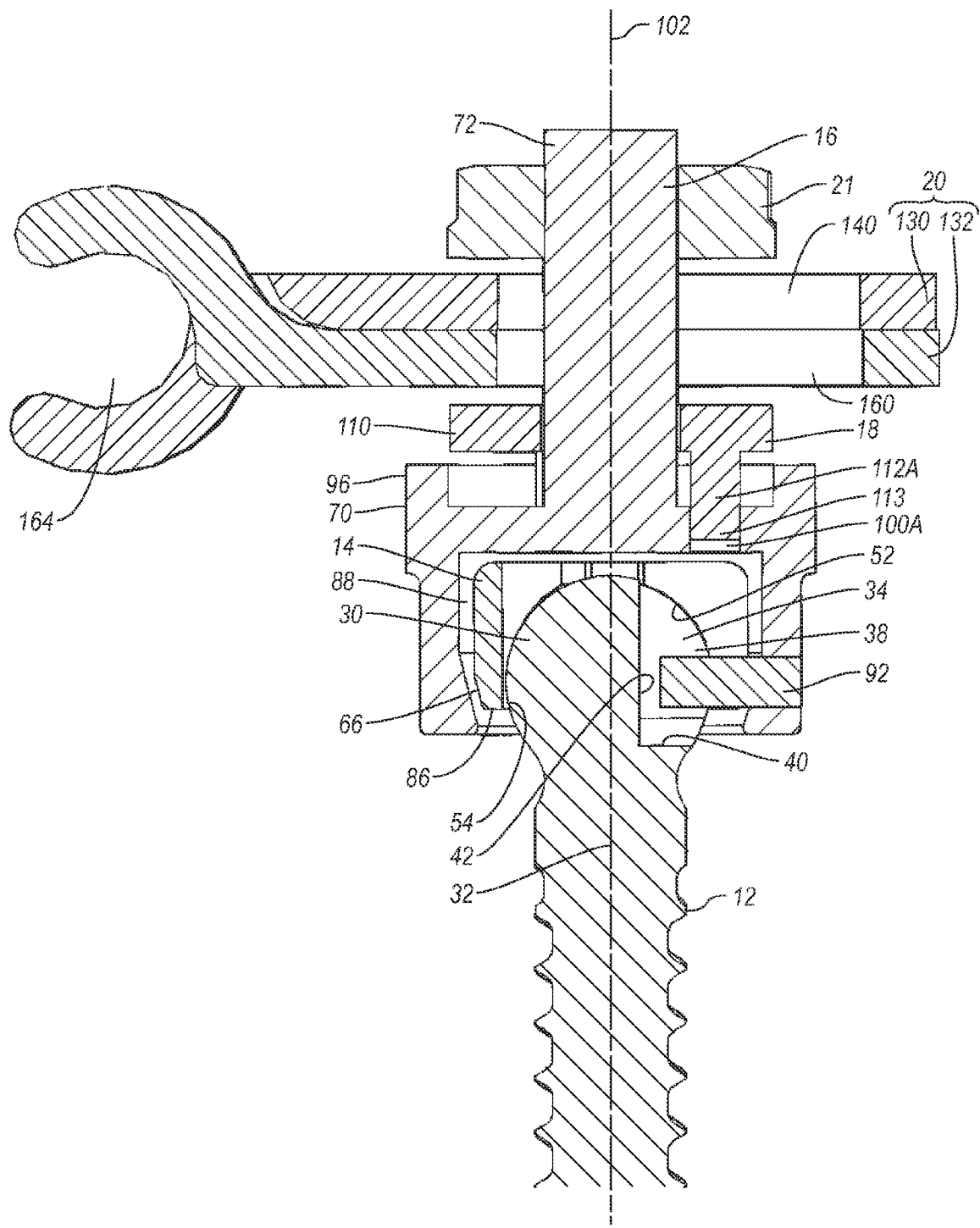
FIG. 14 is a cross sectional side view of the polyaxial screw system shown in FIG. 1 with the drive body in an unlocked position.

A recessed pocket 52 is centrally formed on second end wall 50. Pocket 52 is bounded by an interior surface 53 and has a configuration substantially complimentary to head 30 of screw 12. Pocket 52 is undercut having a configuration that is slightly more than semispherical. As a result, body 44 comprises a substantially annular lip 54 that radially, inwardly projects into pocket 52 at or adjacent to second end wall 50 so as to form a constricted opening 56 to pocket 52. In this configuration, head 30 of screw 12 can be snap-fit into pocket 52 with lip 54 preventing unwanted separation between screw 12 and collet 14 (FIG. 14). Due to the complimentary configuration between pocket 52 and head 30, collet 14 can freely pivot on head 30. In alternative embodiments, it is appreciated that lip 54 need not completely encircle opening 56 but can comprise a plurality of spaced apart sections that capture head 30 within pocket 52. Furthermore, head 30 need not be completely spherical but can be truncated or have a recess formed on the top end thereof.

As also depicted in FIGS. 4-6, an opening 58 is centrally formed on first end wall 48 so as to extend to recessed pocket 52 Likewise, a channel 60 extends through side wall 46, first end wall 48, and second end wall 50 so as to communicate with pocket 52 and openings 56 and 58. As a result of channel 60, collet 14 has a substantially C-shaped configuration when viewed in a top or bottom plan view. A plurality of radially spaced apart slots 62, extend through first end wall 48 beginning at opening 56 and extending out toward side wall 46. Slot 62 continues along interior surface 53 of pocket 52 down to second end wall 50. In the embodiment depicted, slots 62 are recessed on interior surface 53 of side wall 46 but do not extend through side wall 46. In alternative embodiments, slots 62 can extend through a portion of side wall 46. Slots 62 act in conjunction with channel 60 to enable collet 14 to radially, outwardly dilate and also radially, inwardly constrict when radial inward and outward forces are applied collet 14. For example, collet 14 resiliently, outwardly expands or dilates when head 30 of screw 12 is snapped-fit within pocket 52 and, as will be discussed below in greater detail, resiliently, inwardly constricts when collet 14 is used to lock screw 12 relative to drive body 16. It is appreciated that other configurations and orientations of slots 62 and/or channel 60 can be formed on collet 14 to enable collet 14 to selectively dilate and constrict.

Figure 7:
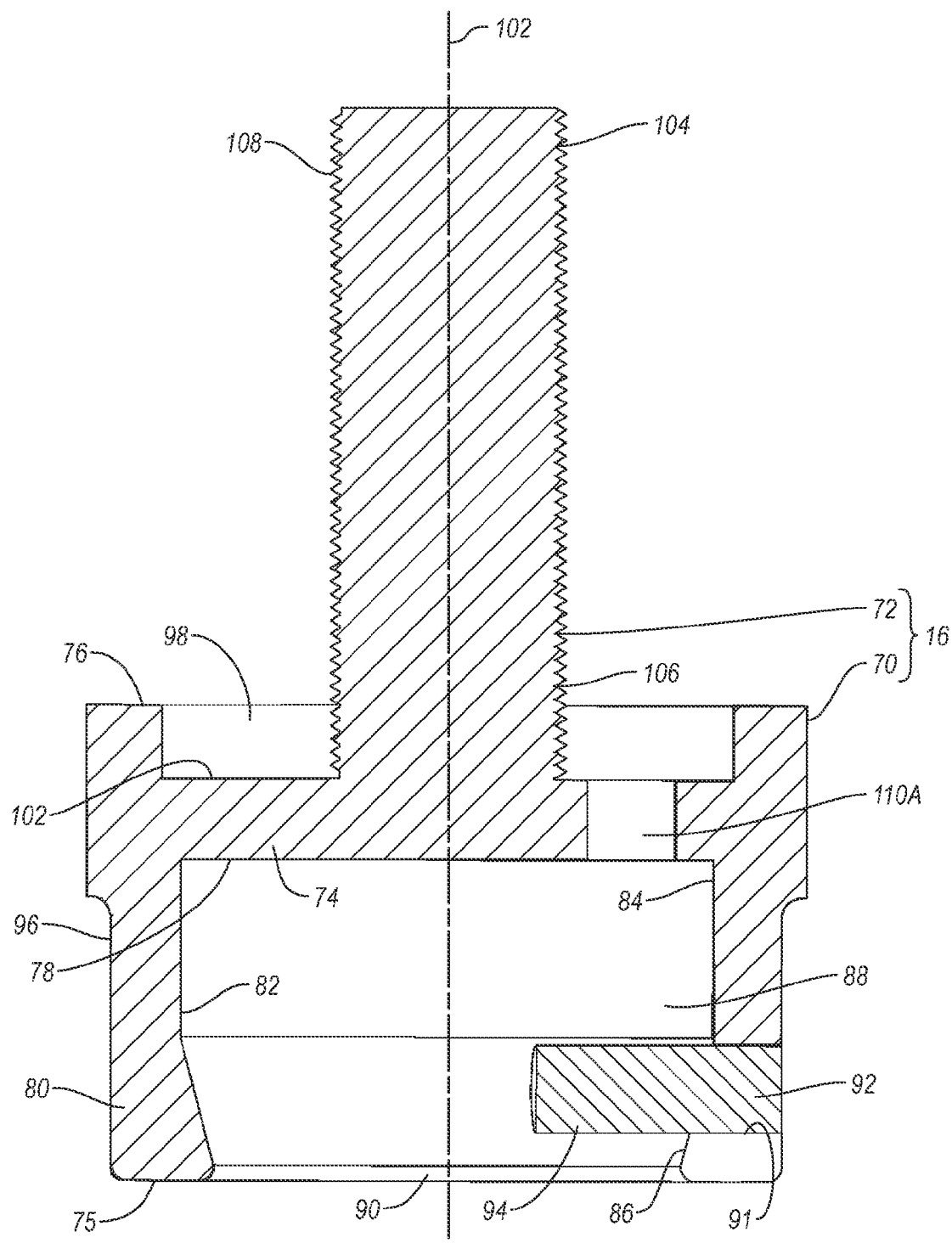
FIG. 7 is a cross sectional side view of the drive body shown in FIG. 2.

Turning to FIG. 7, drive body 16 comprises a drive cap 70 having a shaft 72 projecting therefrom. Drive cap 70 comprises a partition wall 74 having a first side 76 and an opposing second side 78. A tubular sleeve 80 outwardly projects from second side 78 of partition wall 74 and terminates at an annular terminal end face 75. Sleeve 80 has an interior surface 82 that combines with second side 78 of partition wall 74 to bound a socket 88. Interior surface 82 has a first end 84 at which partition wall 74 is formed and an opposing second end 86 at which an opening 90 is formed for socket 88.

Figure 8:
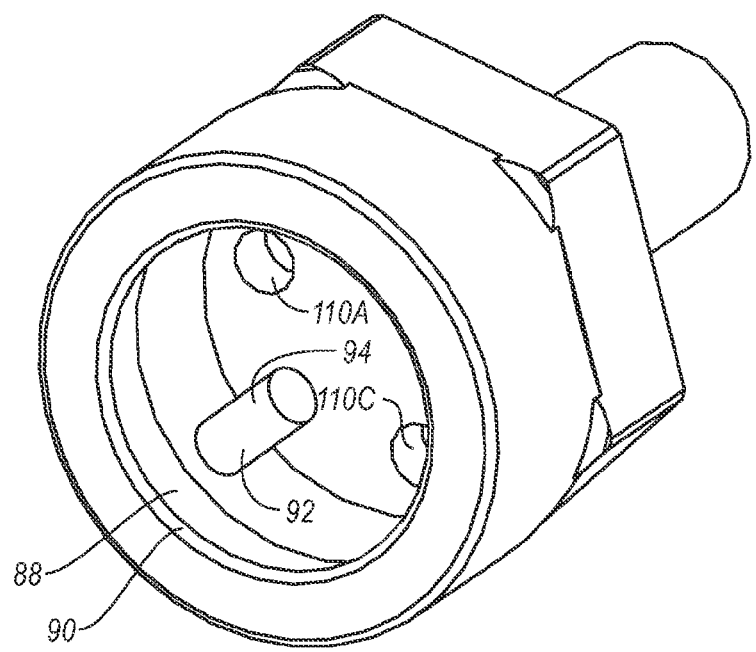
FIG. 8 is a bottom perspective view of the drive body shown in FIG. 7.

In the embodiment depicted, interior surface 82 at first end 84 has a substantially cylindrical configuration that encircles socket 88. Second end 86 of interior surface 82 radially inwardly constricts toward terminal end face 75 so as to have a substantially frustoconical configuration that encircles socket 88. As a result, the diameter at second end 86, and particularly the diameter at opening 90, is smaller than the diameter at first end 84. A passage 91 transversely extends through sleeve 80 at second end 86. As shown in FIGS. 7 and 8, a pin 92 is secured within passage 91 so that a free end 94 of pin 92 projects into socket 88 at second end 86. Pin 92 can be secured within passage 91 by welding, press fit, adhesive, or other conventional techniques.

Figure 9:
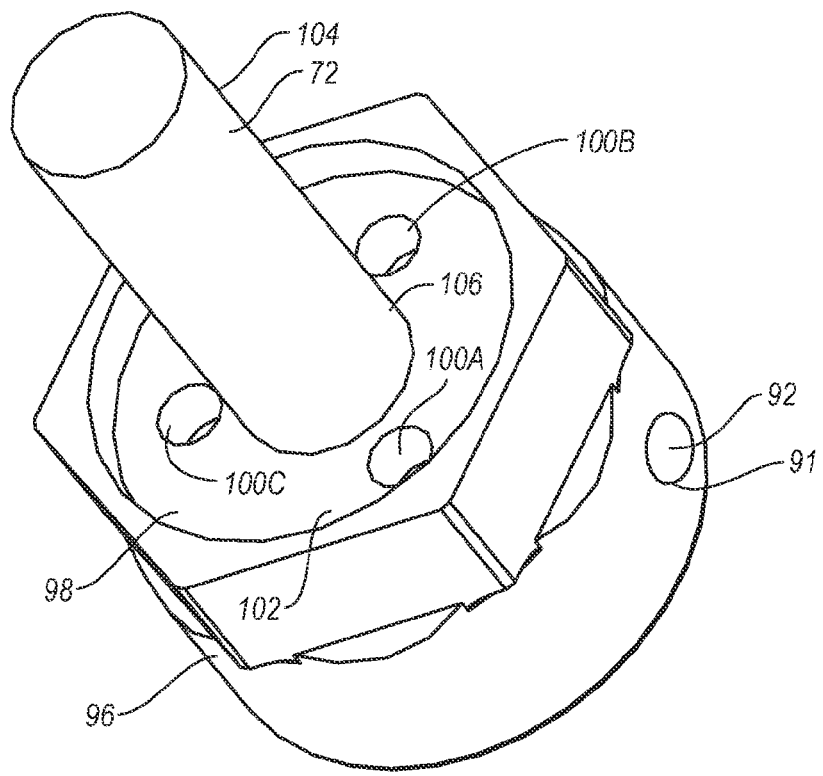
FIG. 9 is a top perspective view of the drive body shown in FIG. 7.

As shown in FIGS. 7 and 9, an annular recess 98 having a floor 102 is formed on first side 76 of partition wall 74 and encircles shaft 72. A plurality of spaced apart passageways 100A-C pass through partition wall 74 by extending from floor 102 of annular recess 98 to socket 88. Passageway 110A is generally illustrated in FIG. 7 as being vertically aligned with pin 92 for ease in illustration of the different parts. In practice, however, for reasons as will be discussed below in greater, passageway 110A-C are typically off set from pin 92 as shown in FIG. 9. Drive cap 70 also has an exterior surface 96 that encircles drive cap 70 and extends from first side 76 of partition wall 74 to terminal end face 75. A portion of exterior surface 96 toward first side 76 has a polygonal or irregular configuration. As a result, a tool, such as in the form of a socket or wrench can be used to engage drive cap 70 to facilitate rotation thereof. In alternative embodiments, it is appreciated that various slots, openings, recesses and/or other contours can be formed on drive cap 70 to enable engagement with a specially designed tool to facilitate rotation of cap 70.

Shaft 72 centrally projects from partition wall 74 and extends between a first end 104 and an opposing second end 106. As shown in FIG. 7, shaft 72 has one or more helical threads 108 encircling and formed along the length of shaft 72 for threaded engagement with fastener 21. A central longitudinal axis 102 centrally extends through drive body 16 so as to centrally extend through shaft 72.

Figure 10:
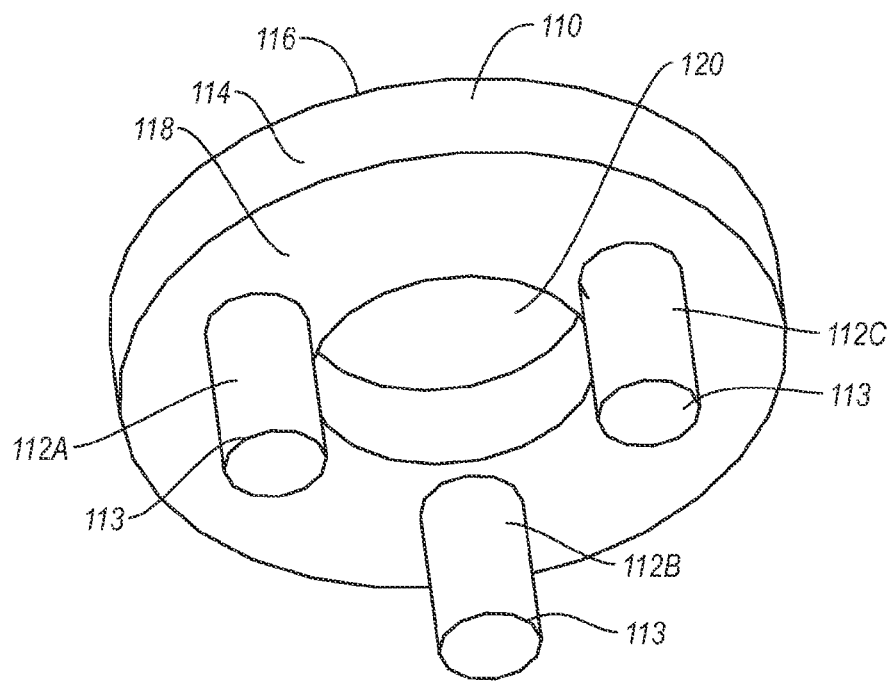
FIG. 10 is a bottom perspective view of the compression cap shown in FIG. 2.

Returning to FIG. 2, compression cap 18 comprises a base 110 having a plurality of arms 112A-C projecting therefrom. More specifically, as depicted in FIG. 10, base 110 has a substantially circular disk shaped configuration with a side wall 114 extending between a top surface 116 and an opposing bottom surface 118. An opening 120 centrally extends between top surface 116 and bottom surface 118 and is sized to permit shaft 72 of drive body 16 to pass therethrough. Base 110 is configured to be received within recess 98 of drive body 16 (FIG. 15). Likewise, each of arms 112A-C are configured to be received within corresponding passageways 100A-C on drive body 16 when base 110 is received within recess 98. Arms 112A-C each terminate at a free end 113 have a length longer than the length of passageways 100A-C. As a result, free end 113 of each arm 112A-C can pass down through passageways 100A-C and project into socket 88 (FIG. 15).

In alternative embodiments, it is appreciated that the plurality of arms 112A-C can be replaced with one larger arm, two spaced apart arms, or four or more arms. Passageways 100A-C would be modified accordingly. Likewise, base 110 can have a substantially C-shaped configuration or compression cap 18 can be divided into two or more separate parts, each part comprising a portion of base 110 and having one or more arms projecting therefrom. In still other embodiments, arms 112A-C can be separate from base 110 or base 110 can be eliminated and rod clamp 20 can be used to press arms 112A-C in passageways 100A-C.

Figure 11:
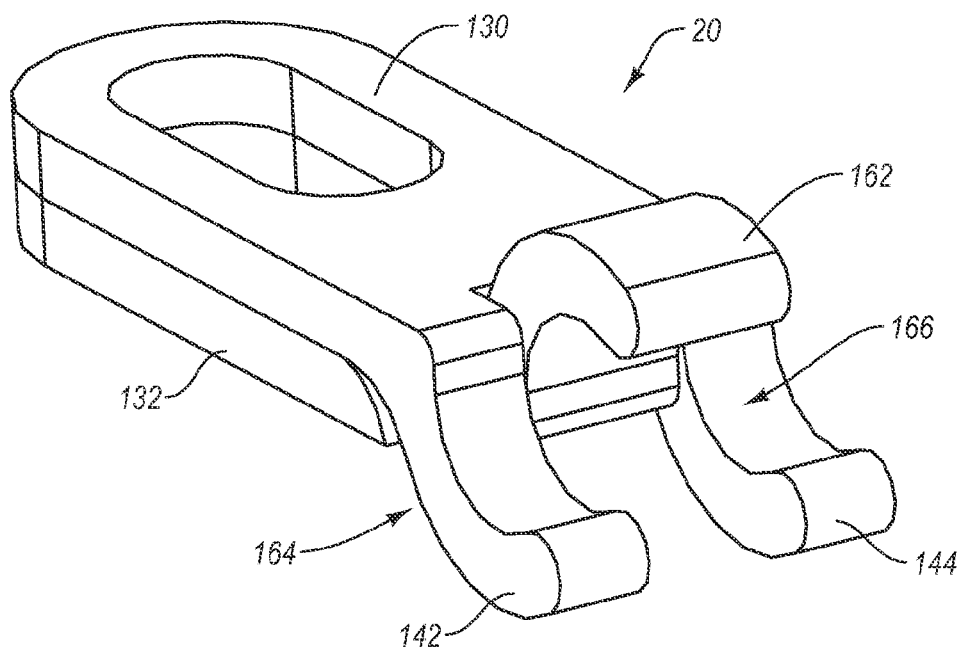
FIG. 11 is a perspective view of the rod clamp shown in FIG. 2.
Figure 12:
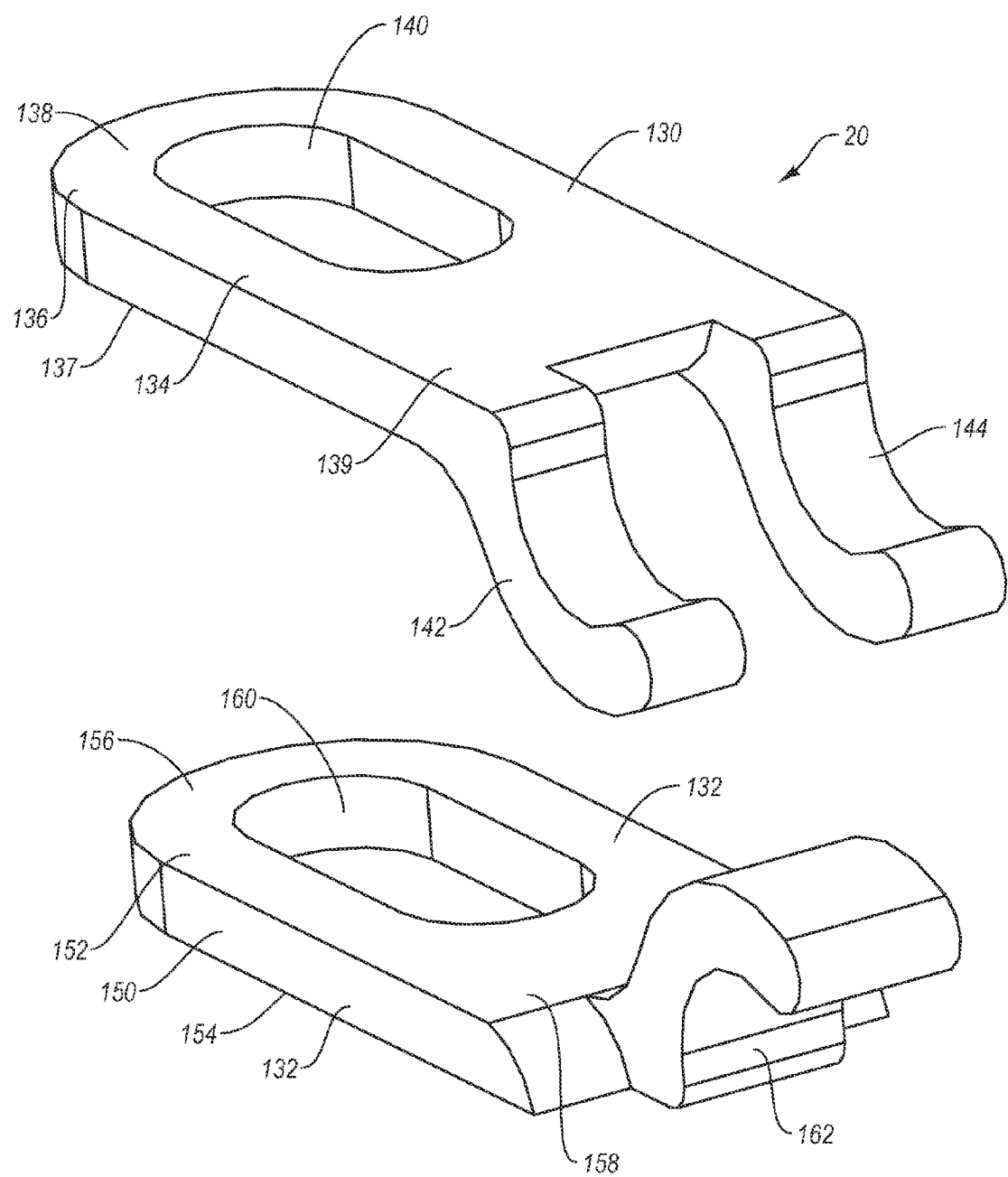
FIG. 12 is a disassembled perspective view of the rod clamp shown in FIG. 11.

Turning to FIGS. 11 and 12, rod clamp 20 comprises a first clamp arm 130 and a second clamp arm 132. First clamp arm 130 comprises a plate 134 having a top surface 136 and an opposing bottom surface 137 that extend between a first end 138 and an opposing second end 139. An elongated channel 140 extends through plate 134 between opposing surfaces 136 and 137 and longitudinally extends along the length of plate 134. Channel 140 is configured to enable shaft 72 of drive body 16 to pass therethrough. Two spaced apart arms 142 and 144 each having a generally U-shaped configuration down and outwardly project from second end 139 of plate 134.

Similarly, second clamp arm 132 comprises a plate 150 having a top surface 152 and an opposing bottom surface 154 that extend between a first end 156 and an opposing second end 158. Again, an elongated channel 160 extends through plate 150 between opposing surfaces 152 and 154 and longitudinally extends along the length of plate 150. Channel 160 is also configured to enable shaft 72 of drive body 16 to pass therethrough.

A singular arm 162 having a substantially U-shaped configuration and inverted relative to arms 142 and 144 projects up and outwardly from second end 158 of plate 150. Clamp arms 130 and 132 are designed to nest together as depicted in FIG. 11 with arm 162 being received between arms 142 and 144. In this configuration, arms 162, 142, and 144 combine to form a locking jaw 164 having a mouth 166 formed therebetween. Jaw 164 is configured to lock a rod 168 (FIG. 1) within mouth 166. That is, by separating first ends 138 and 156 of clamp arms 130 and 132 while retaining second ends 139 and 158 together, mouth 166 of jaw 164 is widened in the same fashion that shears of a scissor are separated. Once in this enlarged position, rod 168 can be positioned between arms 142, 144 and arm 162. Clamp arms 130 and 132 can then be pressed back together causing arms 142, 144 and arm 162 to bias or clamp on opposing sides of rod 168 and thereby lock rod 168 in place. The U-shaped contour of arms 142, 144 and 162 can be generally complimentarily to the diameter of rod 168 to facilitate capturing of rod 168 between the arms.

Returning back to FIG. 2, in the embodiment depicted fastener 21 comprises a threaded nut having a side wall 172 that extends between a top surface 174 and an opposing bottom surface 176. Side wall 172 typically has a polygonal, oval or some other irregular configuration that would enable a tool to selectively engage and rotate fastener 21. A threaded opening 178 extends through fastener 21 from top surface 174 to bottom surface 176. Opening 178 is configured to threadedly engage shaft 72 so that fastener 178 can selectively advance along the length of shaft 72 by being rotated thereon.

Figure 13:
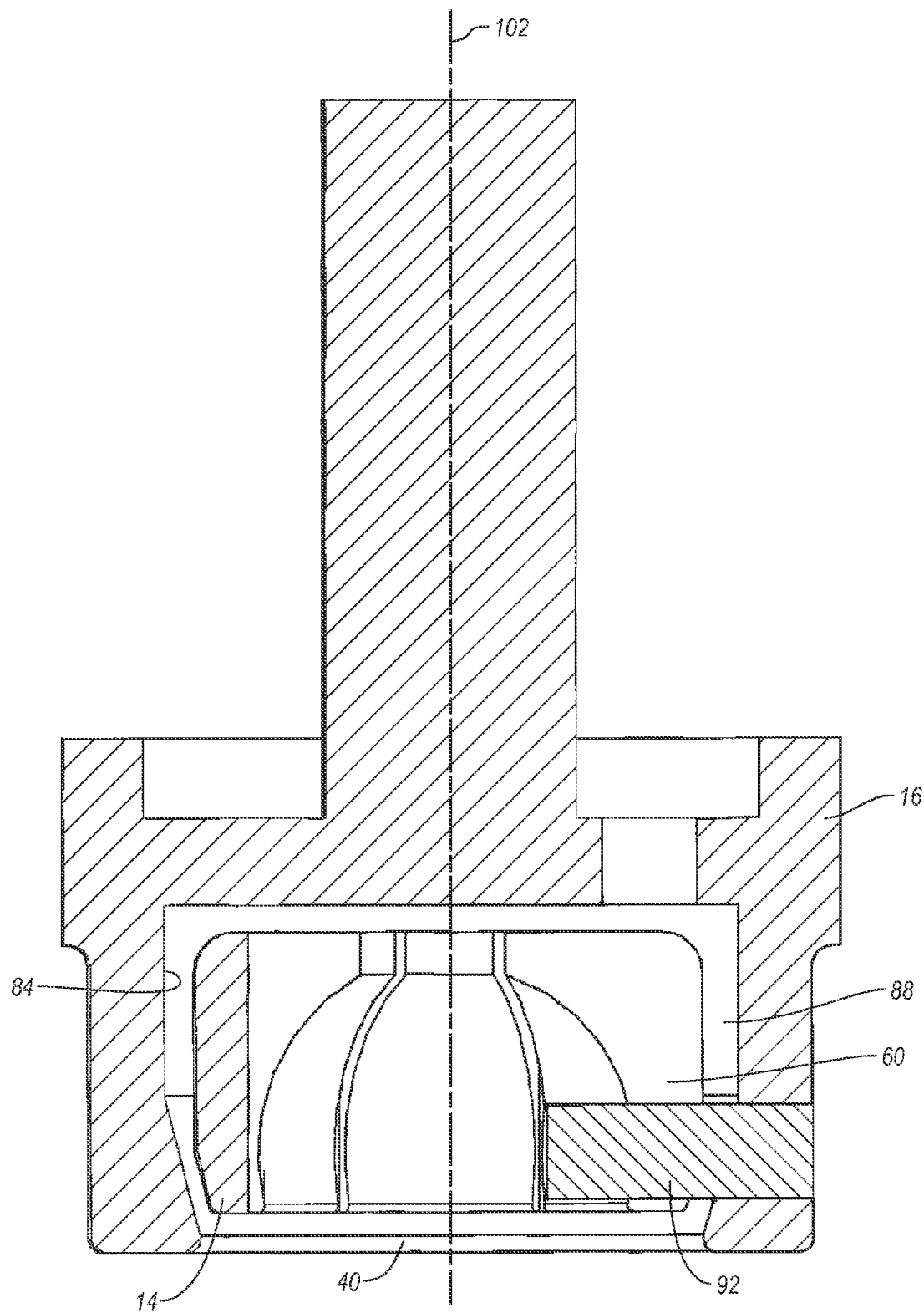
FIG. 13 is a cross sectional side view of the collet shown in FIG. 6 received within the socket of the drive body shown in FIG. 7.

Assembly and operation of polyaxial screw system 10 will now be discussed. Initially, as depicted in FIG. 13, collet 14 is radially inwardly compressed and then inserted into socket 88 of drive body 16 so that pin 92 is received within channel 60 of collet 14. Once collet 14 passes through constricted opening 90 of socket 88, collet 14 resiliently rebounds to its original configuration. In its original configuration, collet 14 has a diameter larger than constricted mouth 90 so that collet 14 cannot unintentionally fall out of socket 88. However, first end 84 of socket 88 is slightly larger than collet 14 so that collet 14 has some free play within socket 88. As a result of pin 92 begin received within channel 60 of collet 14, collet 14 is prevented from rotating within socket 88 about axis 102.

Next, as depicted in FIG. 14, head 30 of screw 12 is snap-fit within pocket 52 of collet 14 so that pin 92 is received within slot 34 of head 30. Again, the annular undercut lip 54 of collet 14 prevents head 30 from unintentionally disengaging from collet 14. However, as a result of head 30 having a complementarily configuration to pocket 54, head 30 is free to pivot within collet 14. Expressed in other terms, collet 14 and drive body 16 can be pivoted in any direction on head 30 of screw 12 when screw 12 is fixedly mounted to a bone. Although drive body 16 can be pivoted relative to screw 12, as a result of pin 92 being received within slot 34, drive body 16 cannot rotate about axis 102 independent of screw 12. Rather, rotation of drive body 16 causes pin 92 to bias against side wall 36 or 38 of slot 34 (FIG. 3) which in turn facilitates concurrent rotation of screw 12.

Accordingly, by using a tool that engages the exterior surface 96 of drive body 16, drive body 16 can be selectively rotated which in turn rotates screw 12 for driving screw 12 into a bone. Again, even after screw 12 is fixed within a bone, drive body 16 and thus shaft 72 can be freely pivoted in any direction on head 30 of screw 12. Once screw 12 is fixed at a desired location, such as on a vertebra or other bone, compression cap 18 can be advanced over shaft 72 so that arms 112A-C of compression cap 18 (FIG. 9) are received within corresponding passageways 100A-C of drive body 16. Coupled clamp arms 130 and 132 can then be advanced onto shaft 72 by advancing shaft 72 up through aligned channels 140 and 160. Fastener 21 is then advanced onto the end of shaft 72. Prior to tightening fastener 21 against clamp 20, clamp arms 130 and 132 are separated as previously discussed and a rod 168 (FIG. 1) is received within the open jaw 164. The ability to pivot drive body 16 relative to screw 12 facilitates alignment of rod 168 with jaw 164. This is particularly true when rod 168 is being connected to a series of polyaxial screw systems 10 that are fixed in a series, such as on sequential vertebra of a spine.

Once rod 168 is in the desired position and drive body 16 is appropriately oriented relative to screw 12, fastener 21 is selectively advanced down along shaft 72. As fastener 21 is advanced down shaft 72, base 110 of compression cap 18 and opposing arms of rod clamp 20 are compressed between fastener 21 and drive cap 70 of drive body 16. As a result of this compression, clamp arms 130 and 132 are pressed together so as to securely engage rod 168 while arms 112A-C are advanced into socket 88 of drive body 16 through passageways 100A-C.

Turning to FIG. 15, as arms 112A-C are advanced into socket 88, free end 113 of each arm 112A-C bias against the top of collet 14 and pushes collet 14 towards opening 90 of socket 88. However, because opening 90 of socket 88 is constricted relative to the size of collet 14, beveled face 66 of collet 14 securely wedges against tapered second end 86 of drive cap 70 and causes collet 14 to radially inwardly compress against head 30 of screw 12. As a result, drive body 16, collet 14, and screw 12 are fixed and locked relative to each other. In turn, by loosening fastener 21 on shaft 72, drive body 16 can again be pivoted on head 30 of screw 12. As previously discussed, passageways 100A-C (FIG. 9) of compression cap 18 are typically rotationally offset from vertical alignment with pin 92. This ensures that arms 112A-C (FIG. 10) that pass down through passageways 100A-C each bias against the top of collet 14 as opposed to one of arms 112A-C aligning with channel 60 of collet 14 and thus not bias against the top of collet 14.

In one embodiment of the present invention, means are provided for securing compression cap 18 to drive body 16 independent of fastener 21. By way of example, prior to positioning collet 14 into socket 88, compression cap 18 can be mounted on drive body 16 with arms 112A-C of compression cap 18 (FIG. 9) being received within corresponding passageways 100A-C of drive body 16 so that the free ends 113 of arms 112A-C are received within socket 88. In this configuration, free end 113 of one or more of arms 112A-C can be slightly bent so that arms 112A-C can still slide within passageways 100A-C but cannot completely pass out through passageways 100A-C. As a result, compression cap 18 is secured to drive body 16 at the time that screw 12 is initially inserted into the bone and does not need to be separately mounted at a later time with rod clamp 20. In other examples of the means for securing, one or more of free ends 113 can be compressed using a press so as to flare out within socket 88. Alternatively, a spot weld or drop of adhesive can be formed at one or more of free ends 113 so as to increase the size of the one or more free ends 113 and thereby prevent free ends 113 from passing back out through passageways 100A-C. Other techniques can also be used.

In still other methods of use, it is appreciated that compression cap 18 can be positioned in its removable state on drive body 16 prior to the time of mounting screw 12 to a bone as long as care is taken to ensure that compression cap 18 does not fall off prior to attaching rod clamp 20 and fastener 21. In yet other methods of use, compression cap 18 can be removably positioned on drive body 16 following which fastener 21 or some other temporary fastener is secured to shaft 72 or is otherwise used to secure compression cap 18 to drive body 16. Screw 12 can then be secured to a bone without the risk of separation of compression cap 18. Once screw 12 is secured in place, fastener 21 or the removable fastener can be removed following which rod clamp 20 is mounted on shaft 72 and fastener 21 is secured on shaft 72 over rod clamp 20. In essence, depending on the type of tool used to drive screw 12 into the bone, all or some of compression cap 18, rod clamp 20 and fastener 21 can be mounted on shaft 72 before or after securing screw 12 to the bone.

Figure 16:
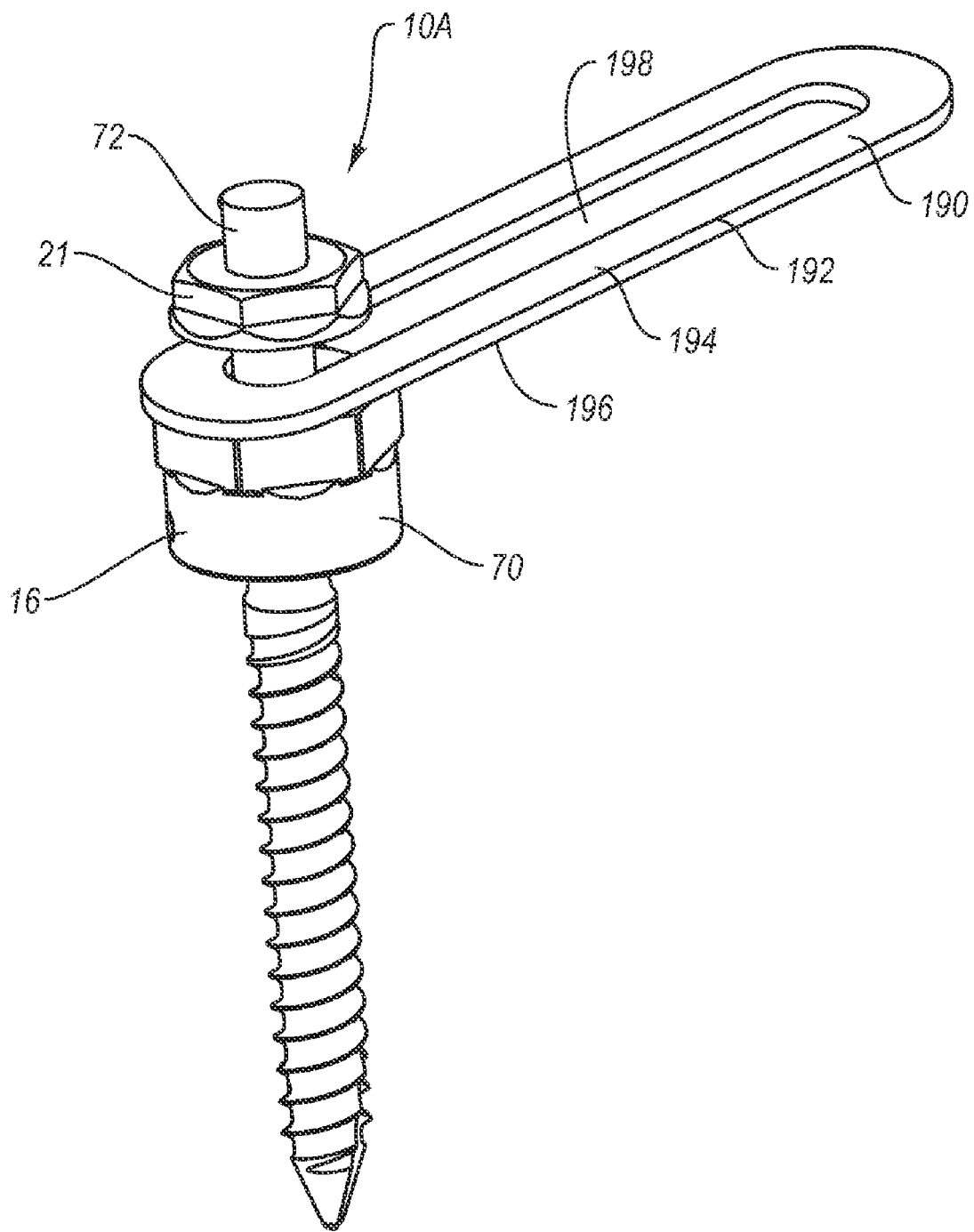
FIG. 16 is an alternative embodiment of the polyaxial screw system shown in FIG. 1 with the rod clamp being replaced by a plate.

It is appreciated that rod 168 will typically be connected to at least one other polyaxial screw system 10 or other type of anchor so as to fix the adjacent vertebra or other adjacent bones relative to each other. It is also appreciated that rod clamp 20 is only one example of a stabilizing structure that can be used with the remainder of polyaxial screw system 10. For example, any other type of rod clamp or mechanism for securing rod 168 that can be secured on shaft 72 can also be used in the present invention. In yet other embodiments, rod clamp 20 can be eliminated and replaced with other types of stabilizing structures that extend between adjacent polyaxial screws. By way of example and not by limitation, depicted in FIG. 16 is one embodiment of a polyaxial screw system 10A. Polyaxial screw system 10A is identical to screw system 10 except that rod clamp 20 has been replaced with a stabilizing structure that comprises plate 190.

Plate 190 comprises an elongated body 192 having a top surface 194 and an opposing bottom surface 196 that extend between opposing rounded ends. An elongated slot 198 extends between opposing surfaces 194 and 196 and extends along the length of body 192. Slot 198 is configured so that shaft 72 can be passed therethrough and so that plate 190 can be pressed between fastener 21 and compression cap 18 or drive cap 70 of drive body 16. In alternative embodiments, it is appreciate that plate 190 can have a variety of different configurations and can have a plurality of spaced apart slots of openings for engaging with a number of different polyaxial screws.

Different embodiments of the present invention have a number of unique features over conventional systems. For example, as a result of using shaft 72 with fastener 21 that completely encircles and screws down on shaft 72, this design has improved mechanical and structural benefits over the prior art polyaxial screws having a U-shaped collar. In addition, as a result of the use of shaft 72, a number of different types of plates, clamps, and other types of connectors and stabilizing structures can be easily used with the inventive polyaxial screw systems. In addition to the foregoing, the inventive systems are also easily mountable and adjustable. Other advantages are also provided by different embodiments of the present invention.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A polyaxial screw system comprising:
    a drive cap comprising:
        a partition wall having a first side and an opposing second side, a passage extending through the partition wall between the opposing sides;
        a sleeve projecting from the second side of the partition wall, the sleeve and partition wall at least partially bounding a socket;
        a shaft outwardly projecting from the first side of the partition wall;
    a screw having a threaded portion and a head formed on an end thereof, the head of the screw being at least partially disposed within the socket of the drive cap;
    a collet at least partially disposed within the socket of the drive cap, at least a portion of the collet being positioned between the drive cap and the head of the screw; and
    a compression cap, at least a portion of the compression cap movably extending through the passage in the partition wall so that the compression cap can selectively move the collet relative to the drive cap.

2. The polyaxial screw system as recited in claim 1, wherein the shaft is substantially cylindrical and has a transverse cross section that is continuously solid.

3. The polyaxial screw system as recited in claim 1, wherein the shaft centrally projects from the partition wall.

4. The polyaxial screw system as recited in claim 1, further comprising a fastener adapted to selectively couple with the shaft, the fastener applying a force to the compression cap.

5. The polyaxial screw system as recited in claim 4, wherein the shaft is threaded and the fastener comprises a nut encircling the shaft and threadedly engaging with the shaft.

6. The polyaxial screw system as recited in claim 4, further comprising a stabilizing structure mounted on the shaft between the fastener and compression cap.

7. The polyaxial screw system as recited in claim 6, wherein the stabilizing structure comprises a rod clamp or a plate.

8. The polyaxial screw system as recited in claim 1, further comprising:
    the head of the screw having a slot formed thereon; and
    a pin projecting from the drive cap into the slot such that rotation of the drive cap facilitates rotation of the screw.

9. The polyaxial screw system as recited in claim 8, wherein the collet has a channel formed thereon, the pin extending through the channel of the collet.

10. The polyaxial screw system as recited in claim 1, wherein the sleeve of the drive cap has an interior surface extending between a first end having the partition wall formed thereat and an opposing second end, the second end bounding an opening for the socket, wherein the interior surface of the sleeve radially inwardly tapers at the second end thereof.

11. The polyaxial screw system as recited in claim 10, wherein the collet has a side wall extending between a first end face and an opposing second end face, the second end face having a pocket formed thereat, at least a portion of the head of the screw being received within the pocket of the collet.

12. The polyaxial screw system as recited in claim 11, wherein at least a portion of the side wall of the collet has an outside diameter that is larger than an inside diameter of the interior surface of the sleeve at the second end thereof.

13. The polyaxial screw system as recited in claim 11, wherein the compression cap comprises:
 a base positioned adjacent to the first side of the partition wall of the drive cap; and
 an arm projecting from the base and extending through the passage of the drive cap.

14. The polyaxial screw system as recited in claim 11, wherein the collet further comprises:
 an opening formed on the first end face and communicating with the pocket; and
 a channel extending through the side wall of the collet so as to communicate with the opening formed on the first end face and the pocket formed on the second end face.

15. The polyaxial screw system as recited in claim 1, further comprising:
 a plurality of passages extending through the partition wall between the opposing sides thereof; and
 the compression cap comprises:
  a base positioned adjacent to the first side of the partition wall; and
  a plurality of arms projecting from the base, each arm extending through a corresponding one of the plurality of passages extending through the partition wall.

16. The polyaxial screw system as recited in claim 1, wherein the collet is selectively movable between a first position wherein the drive cap can freely pivot relative to the head of the screw and a second position wherein the collet is radially inwardly compressed by the drive cap which locks movement of the drive cap relative to the screw.

17. The polyaxial screw system as recited in claim 1, wherein portions of the compression cap are disposed on opposing sides of the partition wall.

18. A polyaxial screw system comprising:
 a drive cap comprising:
  a partition wall having a first side and an opposing second side, a first passage extending through the partition wall between the opposing sides;
  a sleeve projecting from the second side of the partition wall, the sleeve and partition wall at least partially bounding a socket;
  a shaft outwardly projecting from the first side of the partition wall;
 a screw having a threaded portion and a head formed on an end thereof, the head of the screw being at least partially disposed within the socket of the drive cap;
 a collet at least partially disposed within the socket of the drive cap, at least a portion of the collet being positioned between the drive cap and the head of the screw; and
 a compression cap comprising:
  a base positioned adjacent to the first side of the partition wall of the drive cap; and
  a first arm projecting from the base and extending through the first passage of the partition wall so that the compression cap can selectively move the collet relative to the drive cap.

19. The polyaxial screw system as recited in claim 18, further comprising:
 a second passage extending through the partition wall of the drive cap between the opposing sides thereof at a location spaced apart from the first passage; and
 a second arm projecting from the base of the compression cap and extending through the second passage of the partition wall.

\* \* \* \* \*

UNITED STATES PATENT AND TRADEMARK OFFICE
CERTIFICATE OF CORRECTION

Page 1 of 3

PATENT NO. : 8,092,503 B2
APPLICATION NO. : 12/270556
DATED : January 10, 2012
INVENTOR(S) : Felix et al.

It is certified that error appears in the above-identified patent and that said Letters Patent is hereby corrected as shown below:

Title Page, Item #57
Line 8 of the abstract, change "within socket" to --within the socket--

Drawings
Sheet 5, replace Figure 7 with the figure depicted below, wherein the left hand instance of "102" should read "101" and the right hand side instance of "110A" should read "100A"

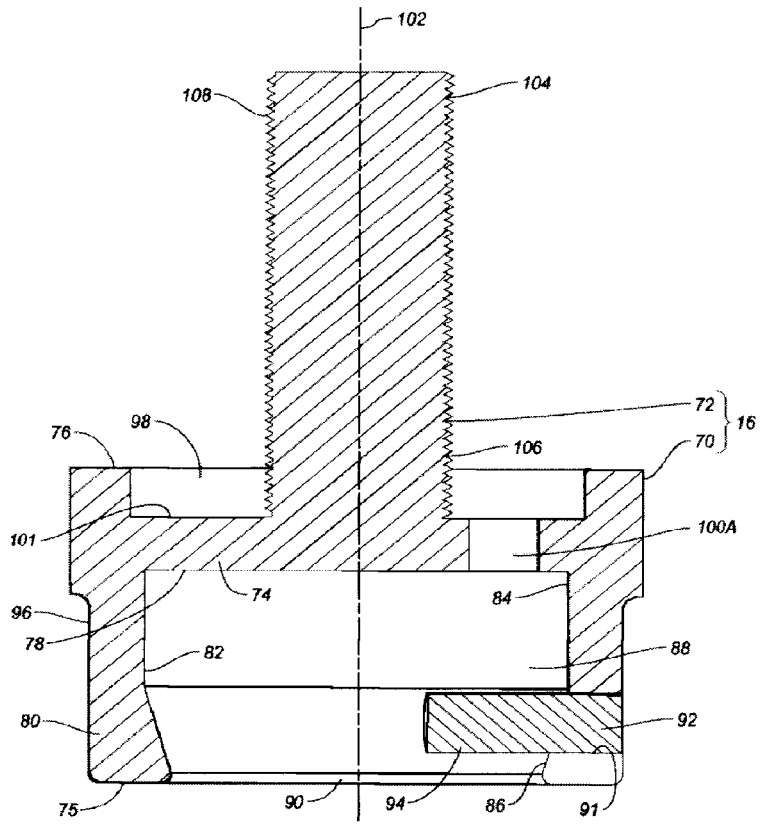

Fig. 7

Signed and Sealed this
Fourteenth Day of August, 2012

David J. Kappos
*Director of the United States Patent and Trademark Office*

CERTIFICATE OF CORRECTION (continued)
U.S. Pat. No. 8,092,503 B2

Sheet 6, replace Figure 9 with the figure depicted below, wherein the bottom middle instance of reference number "102" should read "101"

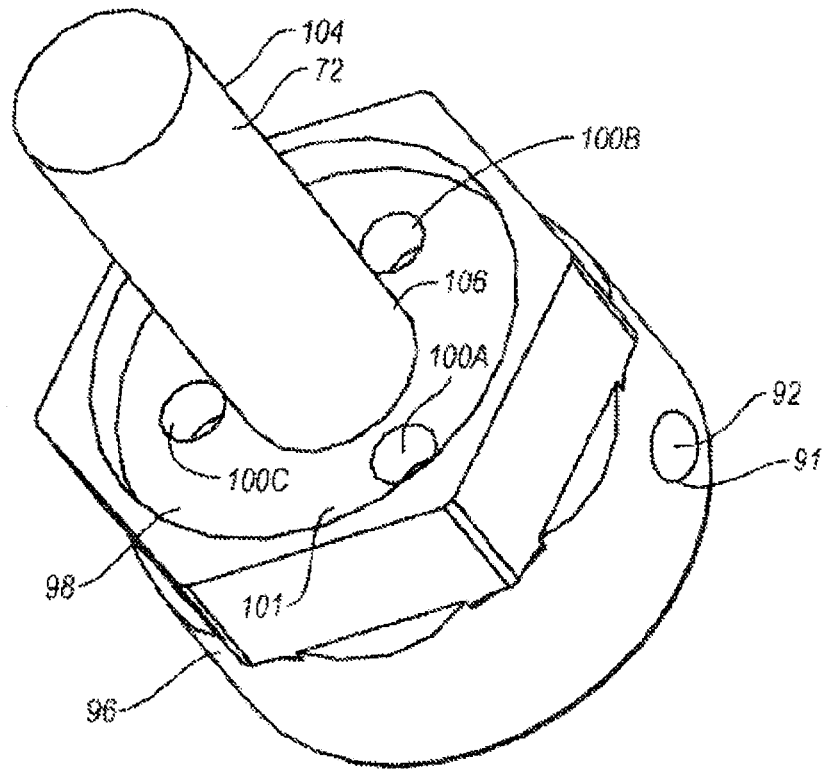

Fig. 9

Column 1
Line 43, change "surgeons" to --surgeon's--

Column 3
Line 33, change "52 Likewise" to --52. Likewise--
Line 47, change "applied collet" to --applied to collet--

Column 4
Line 1, change "radially" to --radially,--
Line 13, change "102" to --101--
Line 16, change "102" to --101--
Line 16, change "110A" to --100A--
Line 20, change "greater, passageway 110A-C" to --greater detail, passageways 100A-C--
Line 26, change "wrench" to --wrench,--
Line 50, change "have" to --having--

Column 5
Line 38, change "depicted" to --depicted,--
Line 46, change "178" to --21--
Line 59, change "begin" to --being--
Line 66, change "54" to --52--

Column 6
Line 29, change "vertebra" to --vertebrae--

Column 7
Line 19, change "16" to --16,--
Line 24, change "removed" to --removed,--
Line 33, change "vertebra" to --vertebrae--
Line 55, change "appreciate" to --appreciated--